United States Patent [19]

Nair

[11] Patent Number: 5,279,949
[45] Date of Patent: Jan. 18, 1994

[54] PROCESS FOR THE ISOLATION AND PURIFICATION OF TAXOL AND TAXANES FROM TAXUS SPP

[75] Inventor: Muraleedharan G. Nair, Okemos, Mich.

[73] Assignee: Board of Trustees operating Michigan State University, East Lansing, Mich.

[21] Appl. No.: 986,368

[22] Filed: Dec. 7, 1992

[51] Int. Cl.$^5$ .................. C12P 17/02; C12N 5/00; C12N 5/02; C07D 305/00
[52] U.S. Cl. .................. 435/123; 435/240.4; 435/240.46; 435/240.48; 549/510; 549/511
[58] Field of Search .................. 549/510, 511; 435/123, 435/240.4, 240.46, 240.48

[56] References Cited

U.S. PATENT DOCUMENTS

| | | | |
|---|---|---|---|
| 4,924,012 | 5/1990 | Colin et al. | 549/511 |
| 4,942,184 | 7/1990 | Haugitz et al. | 549/510 |
| 4,960,790 | 10/1990 | Stella et al. | 549/510 |
| 5,015,744 | 5/1991 | Holton | 549/511 |
| 5,019,504 | 5/1991 | Christen et al. | |
| 5,175,315 | 12/1992 | Holton | 549/510 |

FOREIGN PATENT DOCUMENTS

| | | | |
|---|---|---|---|
| 0336840 | 10/1989 | European Pat. Off. | 549/510 |
| 9207842 | 5/1992 | European Pat. Off. | |
| 9213961 | 8/1992 | World Int. Prop. O. | |

OTHER PUBLICATIONS

Iwakuma, Toshihiro (1992) Idemitsu Sekiyo Kagako K.K. 35, pp. 357-360.
Teresa et al. (1986) Phytochemistry 25, pp. 1185-1187.
Fastre et al (1992) Journal of Liquid Chromotography 15, pp. 697-706.
Zhang et al. (1992) Acta Pharmaceutics Sinca 27, pp. 268-272.
Pavia et al Organic Laboratory Techniques, CBS College Publishing 1982, pp. 488-489.
Habtemariam et al. (1990) Planta Medica 56, pp. 187-189.
Morita et al. (1991) Chem Phar. Bull. 39, pp. 693-697.
Witherup et al. (1989) Journal of Liquid Chromatography 12, pp. 2117-2132.
Zamir et al. (1992) Tetrahedron Letters 33, pp. 5235-5236.
Neto et al. (1992) Planta Medica 58, pp. 464-466.
Gonzalez et al (1990) Phytochemistry 29, pp. 321-323.
Balza et al (1991) Phytochemistry 30, pp. 1613-1614.
Harvey et al. (1991) Journal of Chromatograph. 587, pp. 300-305.
Kelsey et al. (1992) Journal of Natural Products 55, pp. 912-917.
Vidensek et al. (1990) Journal of Natural Products 53, pp. 1609-1610.
Witherup, S., et al., Journal of Natural Products 53, 1249-1255 (1990).

*Primary Examiner*—Douglas W. Robinson
*Assistant Examiner*—Jeffrey J. Sevingny
*Attorney, Agent, or Firm*—Ian C. McLeod

[57] ABSTRACT

A process for the separation of taxanes, particularly taxol, from ornamental yew tissue is described. The process involves a specific solvent mixture of ethanol and water which is between 50 to 80 percent by volume ethanol and decolorizing of the resulting extract using activated carbon containing the crude taxanes. The taxanes are separated from the crude extract by a normal phase chromatographic step which preferably is through vacuum or medium pressure column chromatographic separation, using inexpensive silica gel as an absorbent.

17 Claims, 5 Drawing Sheets

PROCESS FOR THE ISOLATION AND PURIFICATION OF TAXOL AND TAXANES FROM TAXUS SPP

BACKGROUND OF THE INVENTION

(1) Field of the Invention

The present invention relates to a process for the isolation and purification of taxol and other taxanes from Taxus spp plant material by using a particular combination of solvent extraction and normal phase chromatographic purification which produces the taxanes in high yield and purity. The process is particularly characterized in the use of preliminary solvent extraction and purification steps which remove the desired taxanes from the plant material without removing lipid and chlorophyll components which interfere with the chromatographic purification.

(2) Description of the Prior Art

The prior art has described taxol and other taxanes isolated from the bark of Taxus spp. which are useful as chemotherapeutic agents, particularly in the treatment of cancers. Illustrative are U.S. Pat. No. 5,019,504 (1991) to Christen et al and WO 92/07842 (1992) to Rao et al. Christen et al describe a cell culture process using *Taxus brevifolia* for producing the taxanes which are then separated by chromatography, by solvent extraction or adsorption methods. Culturing of plant cells is a difficult method for production of the taxanes for use on a large scale. Rao et al describe a process using reverse phase liquid chromatography. The plant material is extracted with a polar solvent, which is 95% by volume ethanol, for 24 hours at ambient temperatures. The 95% by volume ethanol in this step removes many extraneous lipid components and chlorophyll. A solvent-solvent extraction or partitioning step is then used to remove water soluble materials from the water insoluble taxanes. Various solvents are described for the taxanes (chloroform, benzene, ligroin). The solvent is removed to produce a crude extract. This crude extract is then subjected to the reverse phase chromatography in a solvent mixture to isolate the individual taxanes.

There are multiple problems with the Rao et al process. The most important is that plant lipid components and large quantities of chlorophyll are extracted by 95% by volume ethanol. These lipid and chlorophyll components interfere with the separation in the chromatographic column. Also, the crude product is colored from compounds in the plant material and these color compounds interfere with the chromatographic separation. The plant material is preferably dried to less than 0.5% moisture and ground, which aids in the removal of the taxanes during the initial extraction. Drying the Taxus plant material is an expensive step. The extraction process of Rao produces large quantities of crude extract in which taxol and taxanes are only a minor component. The reverse phase chromatographic separation using the process of Rao et al is such that taxol is not cleanly separated. The mother liquor from the initial separation of the taxol is subjected to additional reverse phase chromatography and recrystallization to separate more taxol. The more polar solvent fractions contain 10-deacetylbaccatin III which can be crystallized to remove this compound and then resubjected to standard chromatography. Multiple reverse phrase liquid chromatographic steps may be necessary in the process of Rao et al.

In another disclosed method (FIG. 2) ligroin is used to remove lipid components. Aqueous methanol removes the crude taxane mixture which is then extracted with less polar solvents to separate taxol and related compounds from 10 deactylbaccatin III. The taxanes can be isolated and recrystallized using the reverse phase chromatography. An aqueous methanol extract is partitioned between water and benzene and then extracted with chloroform and the solvents are removed. Methanol or acetonitrile and water is used in reverse phase liquid chromatography to separate the taxanes.

The procedures of this reference are set forth in FIGS. 1 to 3. None of the procedures provide a clean separation of each of the components in a single pass through a column without a solvent-solvent extraction. Large amounts of various solvents are necessary.

Reverse phase chromatographic separation of impure taxanes from plant materials is very expensive because of the cost of the column materials. Generally reverse phase separation can be used on the bark of Pacific Yew because of the relatively high concentration of taxol; however, other yews contain lesser amounts of taxol and significant amounts of impurities and thus reverse phase chromatography for separation of taxol from the bulk of the yew materials other than Pacific Yew is not practical. There is a great need for lower cost production of taxol.

Reverse phase separation is best where relatively small numbers of compounds in a mixture are to be separated. A preferred material is silica particles coated with octadecyl silane which is expensive. These particles are used in a column usually at high pressures of between about 50 and 6000 psi and usually with a mixture of acetonitrile and water. In reverse phase chromatography the most polar compounds pass through the column the fastest in contrast to normal phase chromatography.

In normal phase chromatography very inexpensive silica gel is used which is about 100 times less than the best reverse phase particles. In normal phase, the silica gel contains silylhydroxide groups (—SiOH) which bind with polar groups of the solute. Thus the more polar compounds move more slowly along the column than less polar compounds. It would be highly desirable to be able to use normal phase chromatography for the separation of taxol and related compounds which are semi-polar; however, to date such columns have not been used because of the large number of polar impurities in the yew plant material, particularly in ornamental yew.

The problem is to simplify the procedures used to produce taxol and other taxane derivatives and reduce the cost using simplified extraction and chromatographic techniques.

OBJECTS

It is therefore an object of the present invention to provide a process for the isolation and separation of taxol and other taxanes from plant materials, preferably fresh material from ornamental yew, in high yield. In particular it is an object of the present invention to provide a process which significantly reduces the cost of production of the taxane derivatives by eliminating the costly drying step, and by reducing the number of steps and the reagents used. These and other objects will become increasingly apparent by reference to the following description and the drawings.

DESCRIPTION OF PREFERRED EMBODIMENTS

Figure 1:
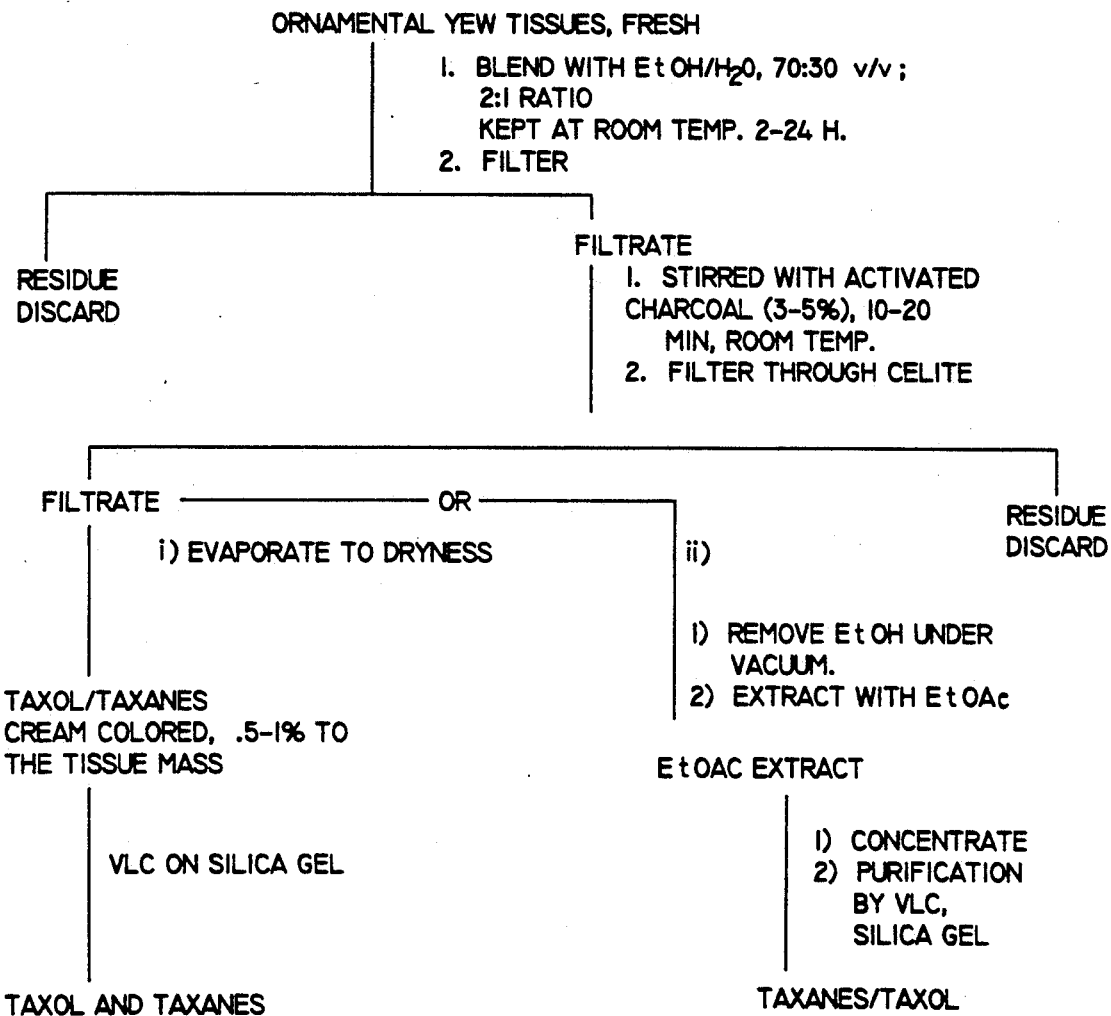
FIG. 1 is a flow chart showing a preferred process of the present invention using activated carbon decolorization and vacuum normal phase liquid chromatography over silica gel.

The present invention relates to a process for extracting and separating taxol and other taxanes from plant material of the genus Taxus which comprises: mixing the plant material with an extracting solvent mixture consisting essentially of between about 50% and 80% ethanol in water mixture by volume so as to extract a crude taxane mixture in the extracting solvent mixture; decolorizing the crude taxane mixture in the solvent mixture with charcoal; removing at least the ethanol from the solvent mixture containing the crude taxane mixture; extracting the crude taxane mixture in a normal phase chromatographic solvent mixture; chromatographically separating taxol and other taxanes in the chromatographic solvent mixture on a normal phase chromatographic column containing silica gel as an absorbent from the crude taxane; separating the taxol and other taxanes from the chromatographic solvent mixture.

Preferably the plant material is from the needles of an ornamental yew. The plant materials are *T. hicksii, T. densiformis, T. gem, T. wardii, T. cuspidata, T. capitata, T. brownii, T. dark green spreader, T. fairview.* The plant material is ground in the extracting solvent mixture.

It is particularly preferred to use fresh rather than dried plant material in order to reduce the cost of extraction. The phrase "dried material" means that the plant material is freeze dried or air dried. The dried material can be used; however, this significantly increases the cost and over time there is a degradation of the taxanes because of the drying step.

It is preferred that the solvent mixture in step (c) be 70% by volume ethanol in water. It is important not to use above 80% by volume ethanol, since lipid components are dissolved by the ethanol. Less than 50% by volume ethanol results in poor extraction of the taxanes.

The decolorization with activated carbon is an important step to avoid problems in the chromatographic separation. Preferably the carbon has been reactivated by heating in a flame.

The normal phase chromatographic solvent mixture is preferably ethyl acetate and hexane in an amount between 10 and 90 percent by volume using gradient separation by increasing the amount of ethyl acetate relative to hexane. Other polar and non-polar solvent mixtures can be used as is well known to those skilled in the art. With these solvents low cost vacuum liquid chromatography on silica gel can be used for the separation. A vacuum is used preferably between about 1 and 15 mm of mercury. The final purification to obtain absolutely pure taxol and taxanes can also be achieved by using low to medium pressure (50-100 psi) normal phase chromatography using tandem columns (columns in series). The solvent in this case is a hexane-ethyl acetate gradient system comprising 100% hexane to 50/50 hexane ethyl acetate to 100% ethyl acetate.

A final separation after normal phase chromatography can also be achieved using reverse phase chromatography. The solvent for reverse phase HPLC separation is usually acetonitrile and water. The acetonitrile is preferably between about 50 and 50 percent by volume of the mixture. The column is operated at 500 to 4000 psi.

The production of taxol from ornamental yew needles and barks at present is not economical due to an extremely high percentage of unwanted impurities carried forward in the extract (40-50% by weight of the dried plant material) during the extraction. This unusually high percentage of impurities in the solvent extract of the needles of ornamental yew makes it very expensive and uneconomical to purify taxol and taxanes from this source in addition to the high cost in drying the needles. Published reports suggest that ornamental yew needles contain about 0.002 to 0.01% of taxol on a dry weight basis (Witherup, S., et al., Journal of Natural Products 53, 1249-1255 (1990)). Organic solvent extraction of 1 kg of the dried ornamental yew needles will afford about 450-500 g of the extract after removing the solvent (45-50% to the biomass) by the published extraction methods using 95% ethanol in water.

Figure 2:
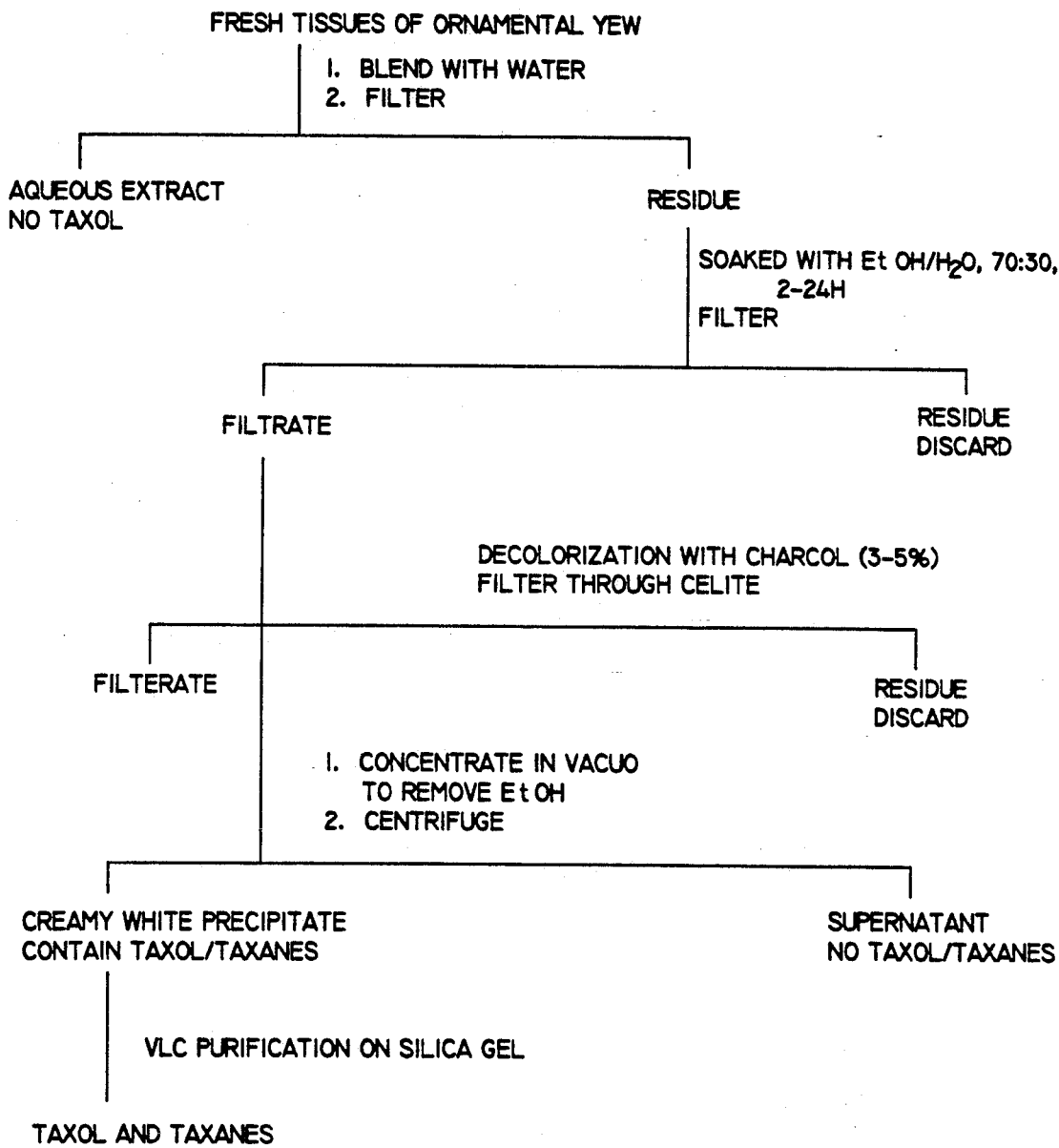
FIG. 2 is a flow chart showing another preferred process of the present invention using activated carbon decolorization and vacuum normal phase liquid chromatography over silica gel.
Figure 3:
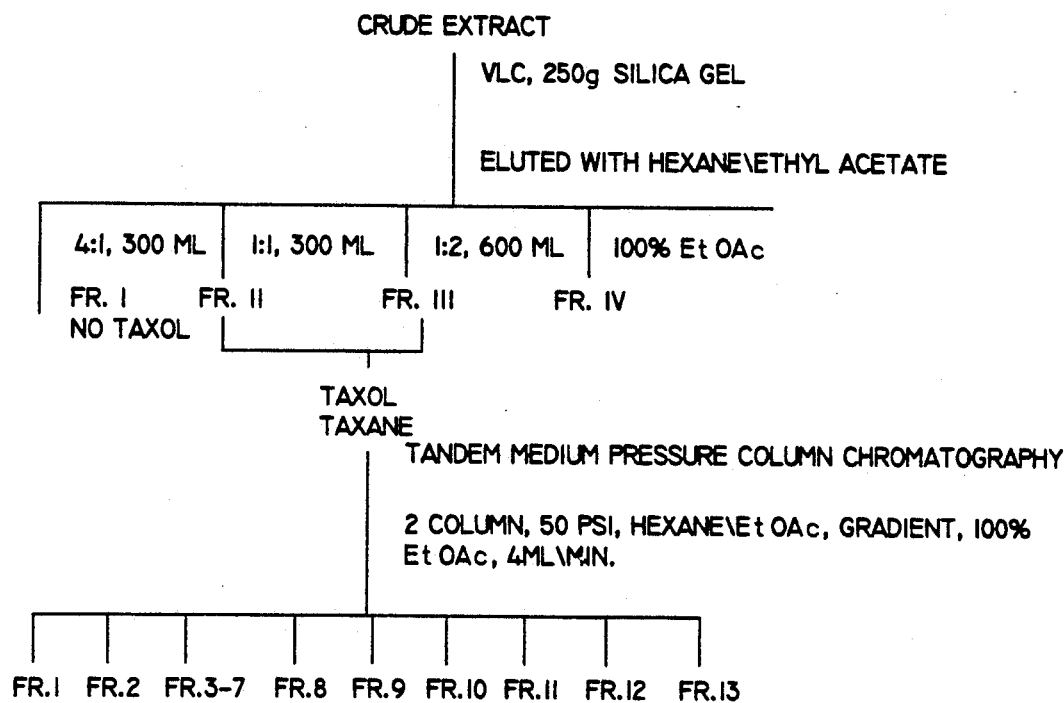
FIG. 3 shows the result of the use of normal phase medium pressure chromatography for separating the products produced by the method of FIG. 1.
Figure 4:
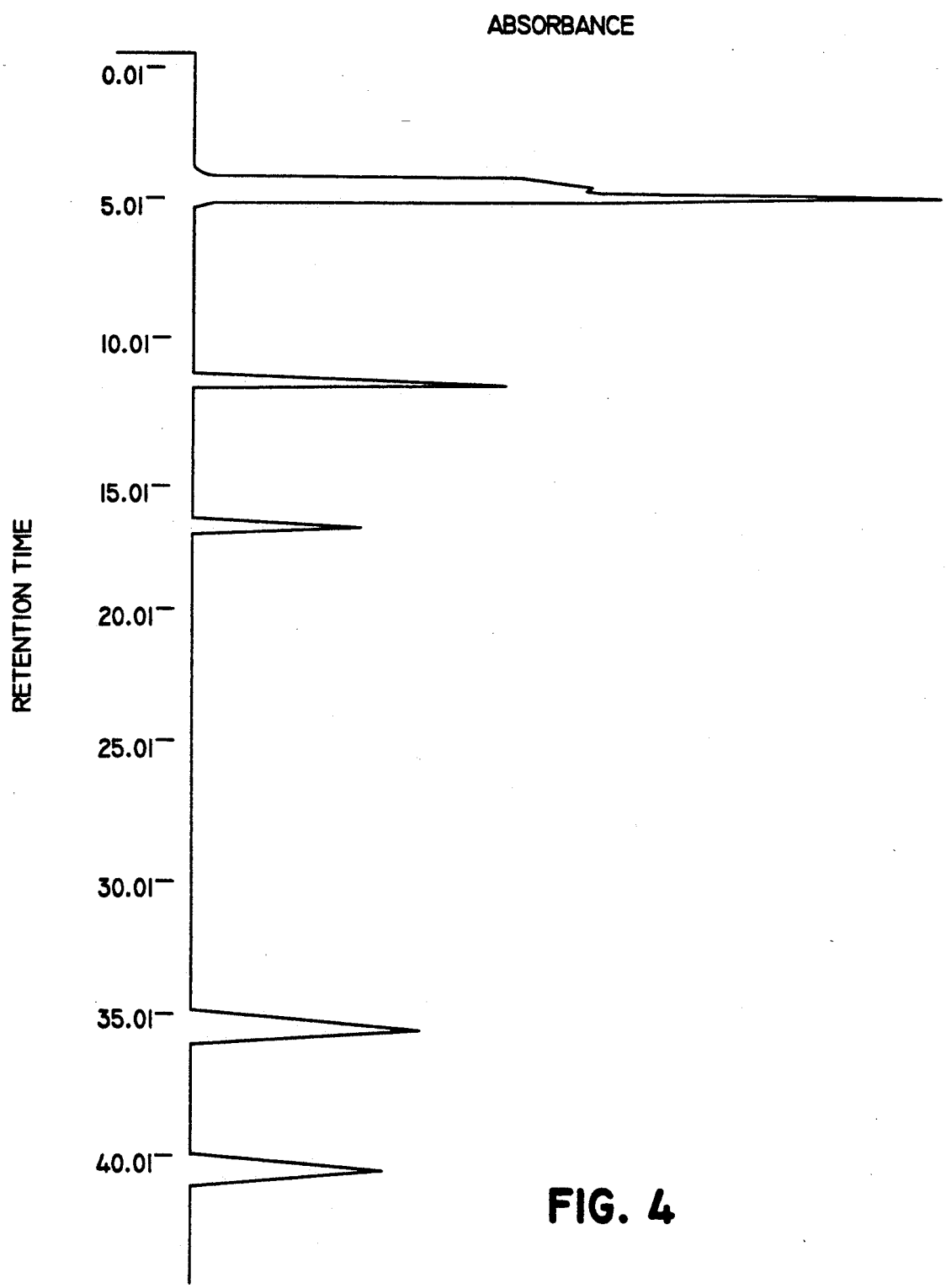
FIG. 4 is a chart showing absorbance versus relative time for reverse phase chromatography of the products of the process of FIG. 3 in Fractions 9 to 11 produced using tandem medium pressure silica column chromatography. The last two fractions are cephalomannine (retention time about 35) and then taxol (retention time about 40).
Figure 5:
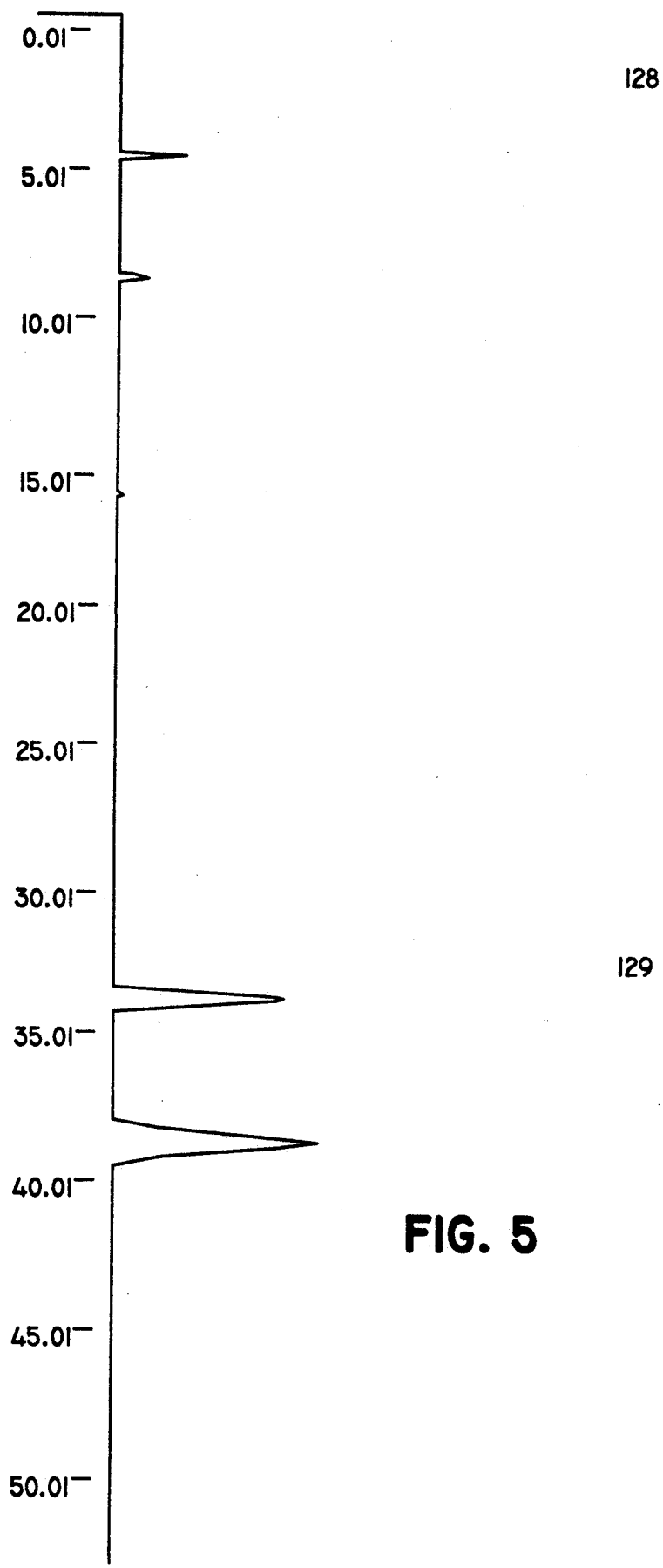
FIG. 5 shows the peaks for cephalamannine (retention time about 35) and for taxol (retention time about 40) for fraction 10 of FIG. 3 showing that the material is taxol and the cephalomannine are produced.

FIGS. 1, 2 and 3 show the extraction step of the present invention which produces 0.5-1% extract of the biomass. FIGS. 4 and 5 show the chromatographic separation achieved by the processes of FIGS. 1, 2 and 3.

The extraction process of the present invention using 50 to 80% ethanol in water retains a large percentage of the impurities in the tissues and does not extract them. Thus the resulting crude product containing taxanes prior to the chromatographic purification step is 0.5 to 1% by weight on a dry basis which is a fraction of the extraction obtained using 95% ethanol and water.

Yew tissues can be needles, stem, bark, whole plant or roots separately or as a mixture. The tissues can be fresh or dried. Use of fresh material eliminates the high cost involved in drying process prior to the extraction of the taxanes. The reported preferred prior art procedure involves the use of dried material since lipophilic solvents are used for the extraction.

Pressing or grinding the fresh tissue with water and removal of the aqueous extract itself is a preferred purification step prior to the extraction since water removes proteins, sugars, and organic and inorganic salts present in the yew tissues. The taxanes are insoluble in water.

In the preferred process, the taxanes are soluble in 70% ethanol and hence the tissues are ground or mixed with 70% aqueous ethanol. The higher percentage of water used in the extraction (compared to the 5% reported by Rao et al) retains the waxes, much of the chlorophyll and lipophilic compounds in the tissue and are not carried into the extract. Usually the plant tissue is soaked for 2 to 24 hours.

The use of activated carbon is very efficient for removing the pigments present in the extract and makes the purification of the taxanes easier and economical. Decolorization with activated carbon does not affect the taxane content of the extract.

The decolorized solution is preferably evaporated to remove ethanol and to precipitate the taxanes which are insoluble in water and then the precipitate is filtered from the solution. The aqueous portion containing the taxane/taxol precipitate can be centrifuged to collect the precipitate of the taxanes. This step also removes all the water soluble impurities carried forward during the extraction with aqueous ethanol. Alternatively, the water can be removed along with the ethanol, although this is not preferred.

The initial separation of taxol and other taxanes is achieved on ordinary inexpensive column silica gel rather than the expensive reversed phase absorbants. Final purification of taxol from the cephalomannine and taxol mixture to obtain 100% purity can be achieved by recrystallization or by purification by medium normal tandem column chromatography using ethyl acetate hexane in a gradient medium pressure silica column. Reverse phase chromatography using a pressure between about 50 and 4000 psi and the "CAPCELL" C-18 particles (Shiseido Co., Ltd., Tokyo, Japan) can also be used for the final separation as shown in FIGS. 4 and 5, although this is expensive. One method uses a 10×250 mm column and a 50—50 mixture by volume of acetonitrile and water at a flow rate of 1.5 ml per minute. The column is operated at 1360 psi. The system uses 0.1 AUFS (absorbance units full scale) at a lambda of 210 mm. In FIG. 4 the first peak is solvent, the second peak is 10 deacetylbaccatin III, the third peak is baccatin III, the fourth peak is cephalomannine and the fifth peak is taxol. FIG. 5 shows only cephalomannine and taxol from fraction 10 in FIG. 3.

EXAMPLE 1

As shown in FIG. 1, fresh clippings of *Taxus hickii* (1.5 Kg) was blended with ethanol (EtOH) (70%, 3L) in a commercial Waring blender (Thomas Scientific, Swedesboro, N.J.) for 3 minutes. The mixture was kept at room temperature for two (2) hours. It was filtered through cheese-cloth and the filtrate was centrifuged (10 minutes, 4° C., 10,000 g) and the supernatant was decanted. The green colored supernatant was mixed with activated carbon (100 g) and stirred at room temperature for 20 minutes. The solution was filtered through celite (diatomaceous earth) in a sintered glass filter. The resulting near colorless solution was evaporated under reduced pressure to remove the ethanol and the aqueous portion was extracted with ethyl acetate (EtOAc) (2×200 ml). The EtOAc was then removed to leave a solid. As shown in FIG. 3, the cream colored solid (3 g) was dissolved in EtOAc (50 ml) and fractionated by silica gel vacuum liquid chromatography (250 g column silica gel) using a hexane EtOAc gradient system ending in 100% EtOAc. The fractions were: I (600 ml, hexane 100%), II (400 ml, 4:1 hexane-EtOAc), III (600 ml, 1:1 hexane EtOAc) and IV (600 ml, EtOAc 100%). Taxol and taxanes were in fraction III by HPLC analysis. Fraction III was further purified by tandem silica gel column medium pressure (30–45 psi) chromatography using a hexane-EtOAc gradient system to obtain pure taxol and taxanes. The fractions from the medium pressure column chromatography were: I (50 ml, 1:1 hexane-EtOAc), II-VII (25 ml each, 100% EtOAc), VIII-XIII (10 ml each, 100% EtOAc), XIV-XV (25 ml each, 100% EtOAc). Fractions I-VII did not contain taxol/taxanes by HPLC analyses. Fractions VIII-X gave white powders upon removal of the solvent and contained pure cephalomannine, taxol and some uncharacterized taxanes. Fractions XI-XIII contained baccatin-III and deacetylbaccatin-III. The individual fractions were separated by HPLC.

EXAMPLE 2

FIG. 2 shows an alternate process wherein the taxols are removed from the water by centrifugation after the EtOH is removed. The taxanes including taxol precipitate since they are insoluble in water. The process is otherwise identical to Example 1.

It is intended that the foregoing description be only illustrative of the present invention and that the present invention be limited only by the hereinafter appended claims.

I claim:

1. A method for extracting and separating taxanes including taxol from plant material of the genus Taxus which comprises:
    (a) mixing fresh clippings of the plant material with an extracting solvent mixture consisting essentially of between about 50% and 80% ethanol in water mixture by volume so as to extract a crude taxane mixture in the extracting solvent mixture;
    (b) decolorizing the crude taxane mixture in the solvent mixture with charcoal;
    (c) removing at least the ethanol from the solvent mixture containing the crude taxane mixture;
    (d) extracting the crude taxane mixture in a normal phase chromatographic solvent containing ethyl acetate;
    (e) chromatographically separating the taxanes in the chromatographic solvent mixture on a normal phase chromatographic column containing silica gel as an absorbent for the crude taxane at a pressure which provides the separation between about 1 mm of mercury and 100 psi;
    (f) separating the taxanes from the chromatographic solvent mixture.

2. The method of claim 1 wherein the solvent in step (a) is 70% by volume ethanol in water.

3. The method of claim 1 wherein the fresh clippings are from an ornamental yew.

4. The method of claim 3 wherein the ornamental yew is selected from the group consisting of *T. hicksii, T. densiformis, T. gem, T. wardii, T. cuspidata, T. capitata, T. brownii, T. dark green spreader, T. fairview.*

5. The method of claim 1 wherein in step (e) an additional column is operated at a pressure between about 50 to 100 psi after the separation at 1 to 15 mm Hg.

6. The method of claim 1 wherein the solvent in step (a) is 70% by volume ethanol in water and the column is operated under a vacuum.

7. The method of claim 1 wherein the taxanes in step (f) are selected from the group consisting of taxol cephalomannine, baccatin-III and 10-deacetylbaccatin III.

8. The method of claim 1 wherein after step (f) the taxanes are separated from each other by a high pressure reverse phase chromatography column of octadecylsilane coated on teflon silica and wherein the solvent mixture is a mixture of acetonitrile and water.

9. The method of claim 8 wherein the chromatographic solvent mixture is about 50% by volume acetonitrile.

10. The method of claim 8 wherein the pressure in the reverse phase chromatography column is between about 50 and 4000 psi.

11. The method of claim 1 wherein the crude extract from step (c) is further extracted with ethylacetate and then the ethylacetate is partially removed prior to step (d) and wherein in step (d) the solvent is the ethylacetate and hexane.

12. The method of claim 1 wherein in step (e) multiple columns containing normal phase silica absorbent are used in series after the separation at 1 to 15 mm Hg.

13. The method of claim 1 where the fresh clippings are ground with water and then the water is removed from the fresh clippings prior to mixing the solvent mixture with the fresh clippings in step (a).

14. The method of claim 1 wherein the fresh clippings are soaked in the solvent in step (a) for 2 to 24 hours at ambient temperatures before step (b).

15. The method of claim 1 wherein in step (c) the crude taxane mixture precipitates in the water remaining after the removal of the ethanol and wherein the crude taxanes are separated from the water.

16. The method of claim 1 wherein in step (c) the water and the ethanol are removed from the crude taxane mixture.

17. The method of claim 1 wherein the fresh clippings are ground in the solvent mixture in step (a).

* * * * *